United States Patent
Jablonski et al.

(10) Patent No.: US 6,765,527 B2
(45) Date of Patent: Jul. 20, 2004

(54) SYSTEM AND METHOD OF RADAR DETECTION OF NON-LINEAR INTERFACES

(75) Inventors: Daniel G. Jablonski, Bethesda, MD (US); Harvey W. Ko, Ellicott City, MD (US); Douglas A. Oursler, Columbia, MD (US); Dexter G. Smith, Columbia, MD (US); David M. White, Sivler Spring, MD (US)

(73) Assignee: The Johns Hopkins University, Baltimore, MD (US)

( * ) Notice: Subject to any disclaimer, the term of this patent is extended or adjusted under 35 U.S.C. 154(b) by 135 days.

(21) Appl. No.: 10/048,769

(22) Filed: Jan. 31, 2002

(65) Prior Publication Data

US 2003/0179126 A1 Sep. 25, 2003

Related U.S. Application Data

(60) Provisional application No. 60/235,624, filed on Sep. 27, 2000.

(51) Int. Cl.[7] .................. G01S 13/04; G01S 7/41
(52) U.S. Cl. ............................ 342/193; 342/22
(58) Field of Search .................. 342/22, 27, 59, 342/193; 340/572.1, 572.2, 551

(56) References Cited

U.S. PATENT DOCUMENTS

| | | | | |
|---|---|---|---|---|
| 4,053,891 A | * | 10/1977 | Opitz | 342/193 |
| 4,439,769 A | * | 3/1984 | Masak | 342/380 |
| 4,586,048 A | * | 4/1986 | Downie | 340/552 |
| 5,191,343 A | * | 3/1993 | Danzer et al. | 342/21 |
| 5,557,283 A | | 9/1996 | Sheen et al. | |
| 6,163,259 A | * | 12/2000 | Barsumian et al. | 340/572.2 |

FOREIGN PATENT DOCUMENTS

| | | |
|---|---|---|
| DE | 27 32 465 | 5/1979 |
| EP | 0 812 028 | 12/1997 |
| GB | 2 351 154 | 12/2000 |

OTHER PUBLICATIONS

PCT Search International Report for PCT/US01/2976, mailed Sep. 16, 2002.

* cited by examiner

*Primary Examiner*—Ian J. Lobo
(74) *Attorney, Agent, or Firm*—Albert J. Fasulo, II

(57) ABSTRACT

A harmonic radar nonlinear junction detector system for detecting concealed weapons, electronics, and other man-made objects utilizing state-of-the art wireless technology, circuit fabrication, signal synthesis, and computer processing techniques to detect and characterize man-made objects possessing nonlinear junctions. The system transmits a pair of low power waveforms and a receiver within the system is coherently tuned to harmonics of the transmitted frequencies of the waveforms to detect man-made metal objects and electronics that contain non-linear junctions. The receiver is also capable of receiving inter-modulation products reflected from the man-made objects that are a result of using two incident signals. The system uses two signal sources generating user-definable waveforms of variable frequencies in order to provide enhanced discrimination and target identification abilities via the processing of returned inter-modulation products.

14 Claims, 1 Drawing Sheet

SYSTEM AND METHOD OF RADAR DETECTION OF NON-LINEAR INTERFACES

CROSS-REFERENCE TO RELATED APPLICATION

This application is a 371 of PCT/US01/29676, filed Sep. 21, 2001 which claims benefit of provisional application No. 60/235,624, filed Sep. 27, 2000.

BACKGROUND

There are certain non-linear impedance characteristics that are an inherent property of man-made objects that contain metal to metal, semiconductor to semiconductor, and metal to semiconductor interfaces. When such man-made objects are illuminated by an electromagnetic signal, the rectification properties of the nonlinear impedances cause new signals to be generated at frequencies that are exact multiples of the frequency of the original signal. These new signals are radiated, and can be detected with a superheterodyne receiver like that used in conventional radars.

A limited number of tactical radar units were developed to exploit these phenomena. One of the earliest is the Metal Target Re-Radiation (METRRA) system developed for the U.S. Army. In this system, three experimental helicopter and vehicle-mounted radars were developed to detect stationary military targets (tanks, vehicles, rifles, and weapon caches) hidden by foliage, a difficult target environment for conventional radar. They successfully demonstrated a one kilometer range capability by transmitting a 400 MHz signal (nominally) and receiving a 1200 MHz signal in return, i.e., the third harmonic.

More recently, a system was developed that incorporated microprocessor technology for signal identification and discrimination. Swept frequency techniques and a directive antenna system were used for determining range. This system was, however, very expensive and had problems associated with nonlinear impedance effects in the electrical connections that linked the transmit circuitry to the antenna array. Without extremely careful, labor-intensive assembly procedures, the system would respond to the harmonics generated within the antenna interface assembly of the device itself and overwhelm or disguise signal responses from legitimate targets.

An even more recent development is a high-power harmonic radar intended for airborne use with large (kilometers) standoff distance. One obvious application for such a system would be the detection of man-made facilities (e.g., drug labs) in supposedly wild jungle areas. However, the success of such a system would be heavily dependent on ambient clutter. In Vietnam, for example, the metal shroud lines used on parachute flares made it possible to detect nonlinear junctions nearly everywhere that U.S. troops had been.

With respect to the problems addressed by the present invention, however, standoff distances are moderate, and power levels need to be comparable to those used in cell phones to stay within safe human exposure limits. None of the aforementioned systems are portable, low power systems that have robust target discrimination capabilities for reliably characterizing manmade objects possessing nonlinear junctions.

What is needed is a radar system that can rapidly detect and reliably identify targets such as concealed weapons and electronics. The targets can be carried by persons either walking through a fixed portal/doorway or walking or congregating in a foyer, entranceway, or other open area. The system needs to be able to achieve a high probability of detection with a low false alarm rate and automatically discriminate between weapons, electronic assemblies and clutter.

SUMMARY

The system proposed for detecting concealed weapons, electronics, and other man-made objects is a harmonic radar nonlinear junction detector. The system utilizes state-of-the-art wireless technology, circuit fabrication, signal synthesis, and computer processing techniques to detect and characterize man-made objects possessing nonlinear junctions.

For convenience, the present invention is referred to as a Concealed Weapon and Electronics Radar (CWER) system. CWER is an advanced harmonic radar transmitting a pair of low power (safe for human exposure) waveforms. A receiver within the CWER system is coherently tuned to harmonics of the transmitted frequencies of the waveforms to detect manmade metal objects and electronics that contain nonlinear junctions. The CWER receiver is also capable of receiving inter-modulation products reflected from the man-made objects that are a result of using two incident signals.

In its most basic operation, a harmonic radar will transmit a single waveform at a nominal carrier frequency of 1 GHz and receive $2^{nd}$ harmonic (2 GHz) returns from electronic devices and $3^{rd}$ harmonic (3 GHz) returns from metal devices. A single frequency system has adequate detection capability with the ability to distinguish between electronic and metal objects. However, its ability to discriminate targets from clutter objects on the person (e.g., keys, coins, zippers, buckles, etc.) or clutter objects in or near by a doorway (e.g., hinges, springs, and doorknobs) is limited. Further, a single frequency system has a very limited capability with respect to classifying different types of targets such as guns and knives.

To address the inherent deficiencies of a single frequency system, the present invention uses two signal sources generating user-definable waveforms of variable frequencies in order to provide enhanced discrimination and target identification abilities via the processing of returned inter-modulation products.

DETAILED DESCRIPTION

Figure 1:
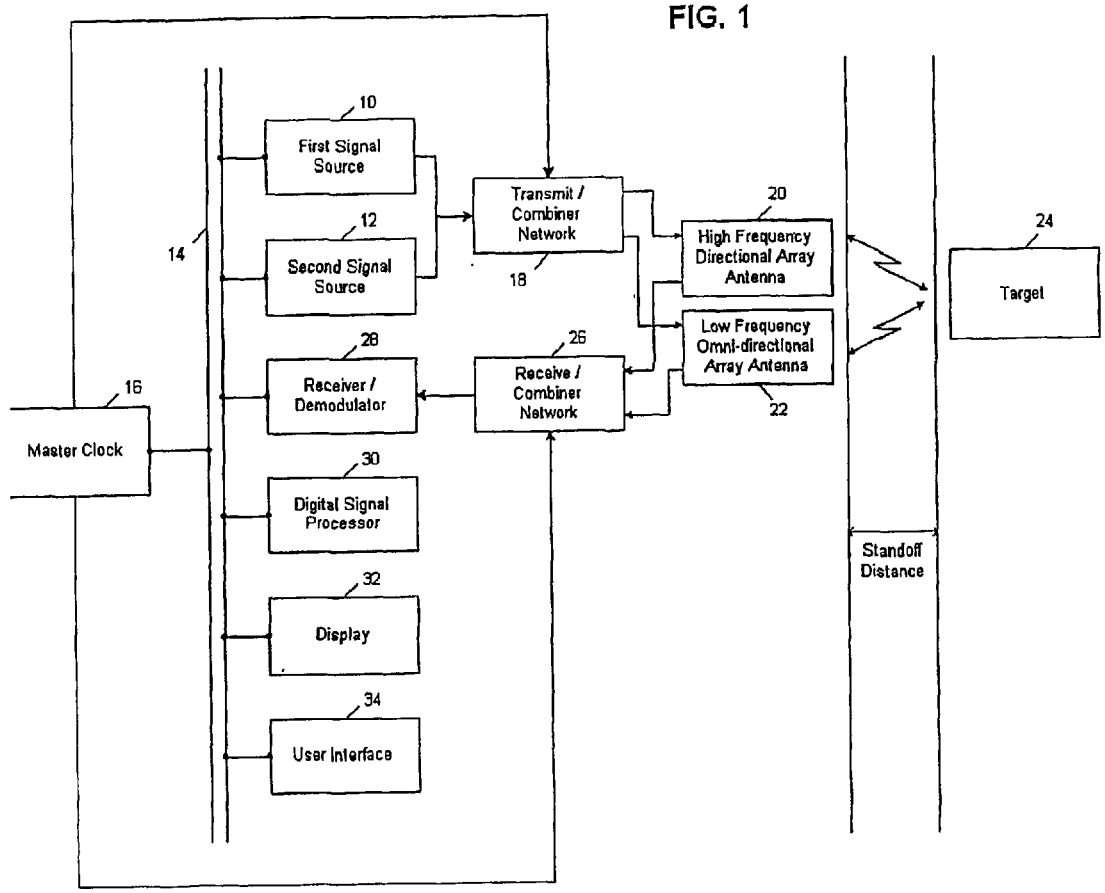
FIG. 1 illustrates a functional block diagram of a CWER system.

The present invention takes advantage of non-linear impedance characteristics that are an inherent property of man-made objects that contain metal to metal, semiconductor to semiconductor, or metal to semiconductor interfaces. Such objects include, inter alia, guns, metal objects comprised of multiple parts mechanically connected, electronic devices, and circuits.

When such objects are illuminated by an electromagnetic signal, the rectification properties of the nonlinear impedances cause new signals to be generated at frequencies that are exactly twice and three times the frequency of the original signal. These new signals are radiated, and can be detected with a superheterodyne receiver like that used in conventional radars. Since these signals are exact harmonics of the original signal, coherent signal detection and integration techniques can be used to yield a huge signal processing gain that can result in a system having extraordinary sensitivity.

In particular, metal to metal interfaces form quantum "tunnel" junctions that exhibit nonlinear voltage-current characteristics that are symmetric with respect to the sign of the voltage and current. Semiconductor junctions have asymmetric current/voltage characteristics. That is, they behave differently for positive applied voltage than for negative applied voltage. The corresponding nonlinear response causes an incident sinusoidal signal to be "squared" for semiconductor interfaces and "cubed" for metal to metal interfaces. That is, if the incident signal is $\sin \omega t$, the nonlinear junction will create and radiate new signals of the form $\sin^2 \omega t$ and $\sin^3 \omega t$. Using standard trigonometry and Fourier theory, it can be shown that this causes the generation of signals at the second (for asymmetric junctions) harmonic and the third (for symmetric junctions) harmonic of the incident signal. That is, signals are generated at frequencies $\sin 2\omega t$ and $\sin 3\omega t$.

Signal reflection is most pronounced for incident signals having a frequency near 1 GHz. At these frequencies, the ambient electromagnetic noise is quite low (near the thermal limit) and low-noise microwave circuitry is readily implemented. At the same time, the wavelength of the incident signal is sufficiently small that efficient antennas are small in size (e.g., inches), and the resolution with which a target can be detected and located is quite good (e.g., feet, not meters). For nominal power levels that are safe for human exposure, detection ranges of several feet are readily achieved. For high power applications, the standoff distance between the system and the target(s) can be extended to hundreds of meters and more.

Referring now to FIG. 1, a CWER system according to the present invention is comprised of at least two signal sources 10, 12 generating a first signal $f_1$ and a second signal $f_2$, respectively. The two signal sources 10, 12 are connected to a data bus 14 and controlled by a master clock 16. The generated signals ($f_1, f_2$) are forwarded to transmit/combiner circuitry 18. The transmit/combiner circuitry 18 then forwards its output to a pair of antennas, a high frequency directional array antenna 20 and a low frequency omni-directional array antenna 22. The antennas then propagate the signals into free space in search of a target 24 having nonlinear characteristics.

When these incident signals contact a target 24 having nonlinear characteristics, the target 24 returns new signals at exact harmonic multiples of the incident signal. The high frequency directional array antenna 20 and low frequency omni-directional array antenna 22 pick up the new signals emanating from the target and send them to receiver/combiner circuitry 26. The receiver/combiner circuitry 26 passes the received signal(s) to a receiver/demodulator 28 that is also connected to data bus 14. Master clock 16 also controls transmit/combiner circuitry 18 and receiver/combiner circuitry 26.

A digital signal processor 30 connected to data bus 14 processes the demodulated received signals. The results from digital signal processor 30 are forwarded to a display 32. A user interface 34 is also included to allow an operator to manipulate the CWER system such as selecting the incident transmission frequencies $f_1$ and $f_2$.

CWER system output to the operator can indicate the category of target detected, its approximate height (high, middle, low) above the floor, and a confidence level (from 1 to 10). For example, GUN-Mid-9 can be displayed to the operator. There can also be a warning notice if multiple targets are detected. Different operator output implementations are possible including, but not limited to, an LCD readout, or audio output units having either wired or wireless connectivity to the CWER electronics unit.

There are at least three CWER implementations designed to enhance security applications. They include a fixed portal unit, a wearable camouflaged unit, and a hand-held portable unit. All three operate at low power, and are below specified human radiation exposure limits. Depending on the implementation and the target, the maximum detection range is approximately 20 to 100 feet.

The fixed portal implementation is designed for entranceways to secure areas such as airport terminals, court houses, and the like. In this case, people wishing to enter the secured area must pass through a portal such as a doorway. This brings the individual within the effective operating range of the system which performs a scan of the person to check if they are concealing any undesired objects. For the fixed portal implementation, the antenna can be, for instance, a flexible strip that can be concealed behind door molding.

The wearable implementation is designed to be worn by security personnel. The unit can be camouflaged as a vest or other article of clothing. The individual wearing the unit is free to walk about with the system actively searching for specific or generic targets. The electronics that comprise the system can be built into the wearable unit and the wearer can be notified of system results discreetly such as via an ear piece connected to the system.

The handheld implementation is not necessarily designed to be discreet. It can be used by security personnel or customs officers in an overt manner to inspect a person, luggage, or the like to see if undesired materials are present. The portable unit would typically be comprised of an antenna probe that can be manipulated by the operator to focus the incident signals as desired. The antenna probe would be coupled to the electronics unit. The electronics unit and a system display would be housed in a portable casing suitable for individual use.

Received signals at the second and third harmonic frequencies are extremely small, (−90 dB) with respect to the power level of the incident signal. However, 90 dB is approximately the spreading loss of a cellular phone signal over one mile. A 600 milliwatt cellular phone signal can easily transmit this distance with a signal bandwidth of 3000 Hz. For a nonlinear junction detector, however, this bandwidth can be reduced considerably, and is limited by dwell-time on target, as opposed to the information content of a voice signal. For targets moving slowly, achievable dwell times will permit signal detection bandwidths of 30 Hz or less, with a corresponding increase in processing gain of 20 dB.

For the expected CWER average transmit power of 300 mW and antenna gain of three (3), the power density one foot from the antenna is 0.08 mW/cm$^2$, which is well below the federally regulated limits. Thus, radiation exposure for a person wearing a CWER unit is below the specific absorption rate (SAR) of 1.6 W/kg of body weight specified for mobile phones because the CWER system power is at or below typical cellular phone power.

Enhanced target discrimination is achieved via the use of multiple digitally controlled microwave signal synthesizers. Using digital synthesizer technology, multiple signal sources can be slaved together so that the nonlinear junction in the target will produce, in addition to the desired harmonic response, a wealth of coherent inter-modulation products. These additional responses, when processed, enhance the ability of a CWER system to detect and discriminate among a wider variety of targets than is currently possible. The use of multiple incident signals, phase modulation, and swept frequency techniques enhances the ability of the CWER system to measure target range and location.

By using a combination of harmonic detection, swept frequency FM techniques, and the use of synthesized generators to generate well-characterized inter-modulation products, sufficient information for separating targets of interest from clutter becomes apparent.

Potential interferents (clutter) include items carried in pockets and purses (e.g., coins, keys, and small pocketknives), metal objects worn (e.g., buckles, zippers, and jewelry) and nearby metal objects (e.g., hinges, springs, and doorknobs). Target discrimination is based on signal amplitude, relation of second to third harmonic, the spectra of inter-modulation products, and range information. Typical target signatures are created by applying the system to known targets and recording the received signal characteristics. Templates for automatic target classification are then developed for implementation into the signal processor of a CWER system.

The antenna and power requirements of the CWER system are a function of the desired target range and intended use. For instance, in a fixed portal implementation, an appropriate antenna is a linear vertical array of broadband dipoles with an omni-directional pattern in the azimuthal plane and directivity in the elevation plane. Elevation plane directivity will allow for identifying a target's height zone above the floor. Planar array antennas are appropriate for handheld and wearable versions of the CWER system, which require both azimuthal and elevation directivity to determine target direction.

The effective radiated power (ERP) (transmit power times antenna gain) is designed to meet the required minimum detectable signal (MDS) for the smallest cross section target. Although the aforementioned METRRA system focuses on military vehicles (tanks and trucks), it does show one harmonic-radar cross section (H-RCS) measurement for a handgun. METRRA expresses H-RCS as a loss term (instead of area) in dB below the incident power. H-RCS loss factor for the handgun is 90 dB below the incident power. For this −90 dB target at a range of 10 meters, a harmonic radar with an ERP of 300 mW and dwelling for 0.1 seconds on a target would have a signal-to-noise ratio of over 40 dB.

The present invention applies at least two incident signals $f_1$, $f_2$, from separate antenna subsystems. This creates inter-modulation products $nf_1 \pm mf_2$, where n and m are integers. The inter-modulation products can readily be distinguished from unwanted harmonics generated within the antennas and related subsystems thereby enhancing the discriminatory detection of actual targets.

Moreover, the response at the various frequencies, $nf_1 \pm mf_2$, can be used to characterize the medium that contains the target. For example, explosives have dielectric constants that differ from those of other materials.

For exploitation of radio frequency carrier phase at frequencies $f_1$ and/or $f_2$, the present invention uses standard techniques based on Tau-dither and or delay-locked loops using standard algorithms in conjunction with digitally controlled oscillators/synthesizers. By measuring relative phase delays between the transmitted and reflected signals, in conjunction with standard ambiguity resolution techniques (which determine how many multiples of signal wavelength lambda must be included in distance computations), these carrier phase techniques can be used to replace or supplement traditional swept frequency and multiple frequency techniques. Using digital synthesizer technology, the phase between signals at $f_1$ and $f_2$ is easily controlled. This yields additional information about the target that would otherwise be lost in an incoherent system.

As mentioned earlier, the largest signal response to nonlinear targets occurs when $f_1 \sim 1$ GHz. However, the advent of high speed personal computers, second and third generation cellular telephones, and ultra-high speed digital data switching technology, is resulting in the widespread use of nonlinear devices that are responsive at frequencies ranging up to 40 GHz.

It is in the $f_1 \sim 10$–24 GHz region where target characteristics, and geometric properties of the enclosures containing the nonlinear target, can best be determined. This is due to the shorter wavelengths and hence higher resolution of the higher frequency signals. In addition, this is a region of the frequency spectrum where microwave dielectric properties of many different types of materials (e.g., explosives) begin to differ from each other, thus permitting the digital signal processor to distinguish and identify various materials of interest.

When $f_2 \sim f_1$, but not equal to $f_1$, then phase and amplitude differences measured simultaneously for both frequencies can provide fine detail about target properties. In particular, the use of two frequencies that are close, but not equal, can assist in ambiguity resolution. This is analogous to, for example, the manner in which a vernier scale on a mechanical caliper or micrometer works.

When $f_2 \ll f_1$, then inter-modulation products are easily detected, and are also easily distinguished from spurious harmonic responses generated within the CWER measuring equipment itself. The lower frequency signal $f_2$ also has the added advantage of deeper penetration into lossy materials, thus allowing for reduced power, and less efficient (but more convenient to use) antenna structures for $f_2$. The efficiency of mixing between signals at ft and $f_2$ in this scenario, and hence the return signal measured by the CWER system, can be used to determine whether certain types of targets, such as, for instance, the fusing device in a landmine, are within their safe (non-powered) or armed (powered) limits. This is because the nonlinear RF characteristics of semiconductor and other nonlinear devices can be a strong function of applied DC voltage. Hence, determinations about the status of the DC voltage used to power a device can be made based on an examination (performed automatically by the digital signal processor in the CWER) of the relative strengths of the generated inter-modulation products.

Moreover, two CWER units having synchronized master clocks and using the Global Positioning System (GPS) can provide antenna aperture enhancement, either in real time or for post processing of stored data. Likewise, this high resolution of timing would permit a single CWER system that is moved with respect to the target to be operated in a synthetic aperture mode, thus increasing the aperture of the CWER systems antennas far above their actual physical size.

With respect to synthetic aperture mode, the spatial resolution (e.g., beamwidth) of an antenna increases as the size of the antenna increases. For nonlinear devices, a way to increase the effective size of the CWER systems antennas without increasing their physical size is to make measurements using two CWER system's operated simultaneously at two different positions of observation of the target (a phased array), or by operating one CWER unit at two different locations at two different points in time (a synthetic aperture).

In both cases, the phase coherence required for successful combination of the signals from the different locations is essential. This coherence can be provided by slaving the internal master clocks in the CWER units to each other, via a wired link, radio link, infrared link, etc., or by locking the individual CWER units to signals from the Global Positioning System or another precise time source. Even commercial radio stations now often broadcast timing reference signals of sufficient precision to permit exploitation of the phase coherence between two CWER units, or between the signals from a single CWER unit, as measured at two locations at two (or more) points in time.

In summary, CWER offers considerable improvements over previous harmonic radars. These improvements include more reliable operation and a robust discrimination capability. The present invention uses surface-mount microwave transmit and receive circuitry, flexible microstrip antennas whose radiation pattern can be digitally controlled, sophisticated flow-soldering techniques, and embedded computer chips. In addition, microwave synthesizer circuitry for generating signals of precise phase and frequency is also utilized. Not only will this permit digital sweeping of frequency for range determination purposes, it will permit the harmonic detection techniques to be expanded to include exploitation of inter-modulation products in new ways.

In the following claims, any means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. A system for detecting and characterizing man-made objects that possess nonlinear junctions in which incident signals are transmitted into free space, and upon contact with said man-made objects that possess nonlinear junctions, said man-made objects that possess nonlinear junctions will reflect new signals that can be received and characterized, said system comprising:

a first signal generator that generates a first incident signal, $f_1$;

a second signal generator that generates a second incident signal, $f_2$, wherein said first incident signal, $f_1$, has a high frequency and said second incident signal, $f_2$, has a low frequency;

transmit circuitry that transmits said first signal, $f_1$, and said second signal, $f_2$;

receive circuitry that is tuned to receive signals that are exact harmonic multiples of said incident signals, $f_1$ and $f_2$, and is also tuned to receive inter-modulation products that are reflected from said man-made objects that possess nonlinear junctions as a result of said man-made objects being illuminated by said incident signals $f_1$ and $f_2$;

an antenna assembly coupled with said transmit and receive circuitry and including a high frequency directional array antenna that assists in the transmission of said first incident signal, $f_1$, and a low frequency omni-directional array antenna that assists in the transmission of said second incident signal, $f_2$, wherein said antenna assembly also assists in the reception of reflected signals from said man-made objects that possess nonlinear junctions;

a signal processor that processes said received reflected signals from said man-made objects that possess nonlinear junctions such that the man-made objects can be characterized according to their composition;

a master clock that synchronizes said first signal generator, said second signal generator, said receive circuitry, said transmit circuitry, and said signal processor; and a data bus that couples said master clock, said first signal generator, said second signal generator, said receive circuitry, said transmit circuitry, and said signal processor together.

2. The system of claim 1 wherein said first signal generator generates a first incident signal, $f_1$, having a frequency of approximately 1 GHz.

3. The system of claim 1 wherein said first signal generator generates a first incident signal, $f_1$, and said second signal generator generates a second incident signal, $f_2$, having a frequency close to but different than that off $f_1$.

4. The system of claim 1 wherein said first signal generator generates a first incident signal, $f_1$, having a frequency within the range of 10–24 GHz.

5. The system of claim 1 wherein said first signal generator generates a first incident signal, $f_1$, and said second signal generator generates a second incident signal, $f_2$, having a frequency much lower than that of $f_1$.

6. The system of claim 1 wherein a second system, having its master clock synchronized to the master clock of the original system via a common timing mechanism, is used to provide antenna aperture enhancement such that the spatial resolution of the systems is increased.

7. The system of claim 1 in which a synthetic antenna aperture enhancement is achieved by operating the system at two different locations at a known time interval with respect to a man-made object.

8. The system of claim 1 further including an operator display for displaying results of the signal processor with respect to man-made objects.

9. The system of claim 1 further including audio output capabilities for notifying an operator of the results of the signal processor with respect to man-made objects.

10. The system of claim 1 further including a user interface for controlling the frequency of the transmitted waveforms.

11. The system of claim 1 in which the system is implemented into a fixed portal.

12. The system of claim 1 in which the system is implemented as a portable wearable unit that can be discreetly worn by an individual and used while the individual moves about an area.

13. The system of claim 1 in which the system is implemented as a portable unit that can be used while moving about an area.

14. The system of claim 1 wherein the signal processor is configured to process said received reflected signals from said man-made objects that possess nonlinear junctions without canceling said received reflected signals from one another.

* * * * *

UNITED STATES PATENT AND TRADEMARK OFFICE
CERTIFICATE OF CORRECTION

PATENT NO. : 6,765,527 B2
DATED : July 20, 2004
INVENTOR(S) : Jablonski et al.

It is certified that error appears in the above-identified patent and that said Letters Patent is hereby corrected as shown below:

Column 8,
Line 24, delete "off" and insert -- of --.

Signed and Sealed this

Thirty-first Day of August, 2004

JON W. DUDAS
*Director of the United States Patent and Trademark Office*